United States Patent [19]

Mills

[11] Patent Number: 4,528,382
[45] Date of Patent: Jul. 9, 1985

[54] IMIDOYL SUBSTITUTED PYRROLES

[75] Inventor: John E. Mills, Hatfield, Pa.

[73] Assignee: McNeilab, Inc., Fort Washington, Pa.

[21] Appl. No.: 442,210

[22] Filed: Nov. 16, 1982

[51] Int. Cl.$^3$ .................................. C07D 207/337
[52] U.S. Cl. .................................. 548/561; 548/539
[58] Field of Search .................................. 548/561, 539

[56] References Cited

U.S. PATENT DOCUMENTS

| 3,952,012 | 4/1976 | Carson | 548/539 |
| 4,238,396 | 12/1980 | Kondo et al. | 548/561 |
| 4,246,176 | 1/1981 | Zaiko | 548/539 |

OTHER PUBLICATIONS

Mills et al., Chem. Abs. 100, 67551g (1984).
Borisov et al., Chem. Abs. 94, 175005y (1981).
Annunziata et al., J. Chem. Soc., Perkins, I, p. 339 (1982).
Organic Reactions, vol. 5, Paul E. Spoerri, Chapter 9, pp. 387-412 (1949).
J. of Scientific and Indust. Research 32 (3), pp. 128-149 (1973), Sambamurthy Seshadri.
Organic Preparations and Procedures Int. 13 (2), 97-101 (1981) de Groot.
J. Org. Chem., vol. 42, No. 26, (1977)—pp. 4248-4251, Julian White and George McGillivray.
J. Chem. Soc., Perkin II, 259 (1982) White and McGillivray.
J. Hetercyclic Chem., 9, 725 (1972), Pinkerton and Thames.
J. Am. Chem. Soc., 72, 876 (1950) Pickard and Vaughan.
J. Am. Chem. Soc. 72, 5017 (1950) Pickard and Vaughan.
J. Pharm. Sci., 60, 1903 (1971) M. A. Luts.
Chem. Reviews, 63, 489 (1963) R. W. Layer.

Primary Examiner—Mark L. Berch
Attorney, Agent, or Firm—David J. Levy

[57] ABSTRACT

Novel compounds, which are aryl-pyrrolyl-imine derivatives of the Formula I

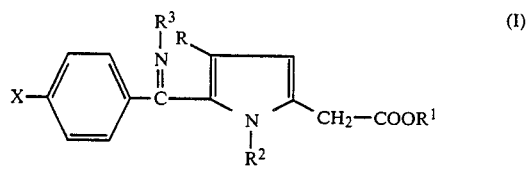

and acid addition salts thereof are disclosed; which compounds may be prepared by the acid catalyzed condensation of an imidoyl chloride with a lower alkyl pyrrole-2-acetate; and which compounds are useful as intermediates to form by hydrolysis, the known useful ketone analogs which have anti-inflammatory and analgesic activity; and certain of which compounds have antisecretory, anti-irritable bowel, antidiarrheal and general behavior effect on the CNS properties.

5 Claims, No Drawings

IMIDOYL SUBSTITUTED PYRROLES

This invention relates to imidoyl substituted pyrroles and is more particularly concerned with aryl-pyrrolyl-imine compounds having the following structural formula I:

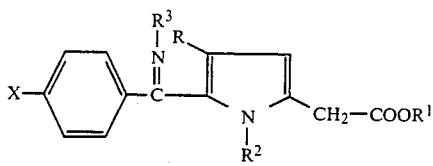

and the acid addition salts thereof, wherein: X is H, $NO_2$, halo, lower alkyl, or lower alkoxy; R is H or methyl; $R^1$ is H or lower alkyl; $R^2$ is H or lower alkyl; and $R^3$ is $C_{1-8}$ straight or branched chain alkyl or $C_{5-8}$ cyclic lower alkyl; and also to the process by which such imines may be prepared by the acid catalyzed condensation reaction of an imidoyl chloride with a lower alkyl pyrrole-2-acetate.

The imines of the present invention and their acid addition salts may be used as intermediates, to form by hydrolysis, the ketone analogs of formula II:

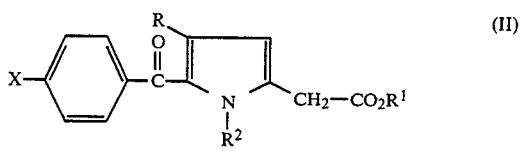

wherein X is H, $NO_2$, halo, lower alkyl, or lower alkoxy; R is H or $CH_3$; $R^1$ is H and $R^2$ is H or lower alkyl, which have been disclosed in U.S. Pat. No. 3,952,012 to Carson as compounds having anti-inflammatory and analgesic activity. They include the drugs tolmetin and zomepirac.

As used herein, "lower alkyl" and "lower alkoxy" may be straight or branch chained saturated hydrocarbons having from 1 to 6 carbon atoms, such as, for example, methyl, ethyl, propyl, isopropyl, butyl, pentyl, hexyl and the like alkyls, and, respectively, the corresponding alkoxys such as methoxy, ethoxy, propoxy, isopropoxy, etc.

As used herein "halo" may be chloro, fluoro, bromo or iodo.

DESCRIPTION OF THE PRIOR ART

Spoerri and DuBois, *Organic Reactions*, 5, 387 (1949), teach that chloroiminium chlorides are formed from nitriles in the acid promoted condensation of nitriles with electron rich aromatic substrates. The intermediate imines in this reaction are normally hydrolyzed to ketones during the work-up, however, nitriles bearing electron withdrawing substitutents have yielded isolable imines. Modifications of the typical reaction conditions have allowed for isolation of the intermediate imines as their hydrochloride salts.

Seshadri, *J. Sci. and Ind. Res.*, 32, 128 (1973), in his review of the Vilsmeier-Haack reaction teaches that iminium species are intermediates in the condensation of activated amides with electron rich aromatic substrates. In this case also, the intermediate iminium species are normally hydrolyzed to ketones under the work-up conditions. Pyrrolyl dimethylformiminium salts have been reported to have been isolated by de Groot, et al., *Org. Preps. and Proc. Int.*, 13, 97 (1981). White and McGillivray, *J. Org. Chem.*, 42, 4248 (1977), have reported the aroylation of a number of pyrroles under Vilsmeier-Haack conditions, but did not isolate the intermediate iminium species.

White and McGillivray, *J. Chem. Soc., Perkin II*, 259 (1982), have recently reported that α-(4-ethoxycarbonyl-3,5-dimethylpyrrol-2-yl)benzylidene-3-chloropropylamine was isolated from the reaction of N-benzoylazetidine with 2,4-dimethylpyrrole-3-carboxylate in the presence of phosphorous oxychloride. They reported that this imine is stable to basic hydrolysis, but is hydrolyzed slowly and incompletely under acidic conditions.

The condensation of lithiated thiophenes with aromatic nitriles was reported by Pinkerton and Thames, *J. Hetercyclic Chem.*, 9, 725 (1972), to yield thienyl aryl ketimines. The condensation of Grignard reagents with aromatic nitriles was reported by Pickard and Vaughan, *J. Am. Chem. Soc.*, 72, 876 (1950), and ibid. 72, 5017 (1950), to yield alkyl-aryl and diaryl ketimines.

Luts, *J. Pharm. Sci.*, 60, 1903 (1971), reported the preparation of a number of N-substituted diaryl ketimines from the condensation of diaryl ketones with primary amines.

Other methods for preparing N-substituted ketimines have been reviewed by Layer, *Chem. Reviews*, 63, 489 (1963).

SUMMARY OF THE INVENTION

This invention relates to the preparation of aryl-pyrrolyl imines of the general formula I given above, wherein X is H, $NO_2$, halo, lower alkyl, or lower alkoxy; R is H or methyl; $R^1$ is H or lower alkyl and $R^2$ is H or lower alkyl; and $R^3$ is $C_{1-8}$ straight or branched chain alkyl, or $C_{5-8}$ cyclic lower alkyl.

Compounds with the above general formula are useful as intermediates in the preparation of 5-aroyl-pyrrole-2-acetic acids having anti-inflammatory and analgesic activity. In addition, some compounds disclosed herein display antisecretory, anti-irritable bowel, antidiarrheal, and general behavior effects on the central nervous system as shown in the following Table I.

The particular acid addition salts of the imines of Formula I may be any desired acid addition salt (from any acid) when their intended use is as an intermediate, but may only be a nontoxic, pharmaceutically-acceptable acid addition salt when meant to be used for their own pharmacological activities, which are shown in Table I.

Examples of suitable nontoxic, pharmaceutically-acceptable acid addition salts include: perchlorate, hydrochloride, sulfate, para-toluene sulfonate, 2-naphthalene sulfonate, methane sulfonate, and other salts of strong acids. For use as an intermediate it is not necessary to use a nontoxic acid addition salt of a strong acid, since any acid addition salt will be suitable, but the preferred salts are the perchlorate and hydrochloride for those uses also.

In some instances the acid addition salts may be isolated as a hydrate, so these are included within the definition of acid addition salts for purposes of the present invention.

The pharmacological activities depicted in the following Table I were obtained by use of the following procedures:

(A) General Behavior: This procedure involves a mouse behavioral assay as described by S. Irwin, *Gordon Research Conference on Medicinal Chemistry*, 1959, p. 133. In this assay, such symptoms as ataxia, decrease in motor activity and loss of righting reflex are observed after intraperitoneal (i.p.) administration in mice of the compound to be tested at doses ranging from 2–1,000 mg/kg body weight.

(B) Glass Bead Test (for relief from discomfort associated with "irritable bowel syndrome"): The glass bead test is carried out with male albino mice of 18–25 grams body weight using groups of five mice for each compound dose tested. The initial screen dose selected for all compounds is 50 milligrams per kilogram of body weight (mg/kg) administered orally in a volume of 0.1 milliliter per 10 grams of body weight. The control groups receive the vehicle, 0.5 percent methocel. The mice are fasted one hour before testing and the test drugs are given one hour prior to glass bead insertion.

At the end of the pretreatment time, the mouse is picked up and held firmly in one hand with his abdomen facing the technician. The glass bead of 3 millimeters in diameter is positioned at the rectum and using a pinching action with a thumb and forefinger, the bead is pushed into the rectum. Then using a glass rod of 3 millimeters in diameter which has been lubricated with 0.5 percent methocel to facilitate insertion, the glass bead is pushed up into the rectum a distance of 2 centimeters using a slow gentle turning motion. The mice are timed as a group using the last mouse inserted as zero time and the number of beads expelled in a group at different timed intervals are recorded. The groups are based on timed intervals of 0 to 5 minutes, 5 to 10 minues, 10 to 20 minutes, 20 to 40 minutes, and greater than 40 minutes. They are given the activity index values of 0, 1, 2, 3 and 4, respectively. Mice who have not expelled their beads by the 40-minute cutoff time are examined for perforations. Those mice whose colons are perforated are eliminated from the group.

The sum of the values divided by the number of mice or beads is termed the activity index for the drug tested. An activity designated as "slight" corresponds to an activity index of 1.0 to 1.9. The results of this test employing oral administration of an imidoyl-substituted pyrrole compound is shown in Table I.

(C) Acute Gastric Fistula Test (demonstrates antisecretory activity): The antisecretory activity of the compound to be tested is studied in female Sprague-Dawley rats after intraduodenal (i.d.) injection of the compound at doses generally ranging from 10–300 mg/kg body weight. The rats are fasted 24 hours before testing and are given water ad libidum while being kept in individual cages. On the day of testing, the rats are weighed and are selected so that the rats in each test have weights within a range of ±20 g.

Surgery is carried out under light ether anesthesia. As soon as the rat is anesthetized its teeth are removed, using a small pinch pliers. A midline incision is made on the abdomen about 1½ cm in length and stomach and duodenum are exposed. If, at this point, the stomach is filled with food or fecal material, the rat is discarded. Using 4–0 suture, a purse string stitch is placed on the fundic portion of the stomach taking care not to pierce any blood vessels in the area. A small nick is made into the stomach in the center of the purse string, and a cannula, consisting of a small vinyl tube with a flange on one end, is put into the stomach and the purse string stitch is closed tightly around the flange. Immediately following this, the test compound is administered i.d. in a volume of 0.5 ml per 100 gm rat. Three rats are generally used for each drug dose tested. Control rats receive the test vehicle, usually 0.5% aqueous methyl cellulose.

After administration of the test compound, the abdominal wall and skin are closed simultaneously with three to four 18 mm wound clips and a collecting tube is placed on the cannula. Each rat is then placed in a box in which a longitudinal slit has been made to allow the cannula to hang freely and to allow the rat to move about unencumbered. After the rat is allowed to stabilize for 30 minutes, the collection tube on the cannula is discarded and replaced with a clean tube to receive the gastric juice. Collections are made at one hour. At the end of the study, the cannula is removed and the rat is sacrificed.

The sample of gastric contents collected is drained into a centrifuge tube and centrifuged to pack down the sediment. Volumes are read and a 1 ml aliquot of the supernatant is put into a beaker containing 10 ml distilled $H_2O$ and is titrated to pH 7 using 0.01 N NaOH. Results are determined for Volume, Titratable Acid, and Total Acid Output where Volume equals total ml of gastric juice minus sediment; Titrable Acid (milliequivalents/l) equals amount of 0.01 N NaOH needed to titrate the acid to pH 7; and Total Acid Output equals Titratable Acid × Volume. Results are reported in % Inhibition vs Controls and a minimum of 5% Inhibition indicates antisecretory activity. An activity designated as "slight" reflects a 33 to 65.9% decrease in total acid output, a "marked" activity indicates a 66 to 100% decrease in this value.

TABLE I

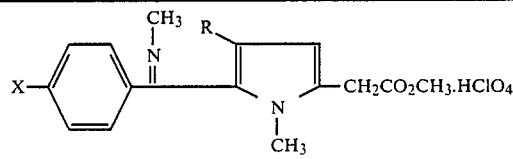

| Compound of Example No. | Above Formula wherein | Screen | Route | Animal | Dose (mg/kg) | Activity |
|---|---|---|---|---|---|---|
| 12 | X = Cl, R = CH₃ | Acute fistula - gastric | ID | Rat | 20 | Marked |
| | | Glass bead | PO | Mouse | 50 | Slight |
| | | General behavior | IP | Mouse | 3–300 | Weak depressant |
| 11 | X = H, R = CH₃ | Acute fistula - gastric | ID | Rat | 20 | Slight |
| 14 | X = CH₃, R = H | General behavior | IP | Mouse | 10–1000 | Weak stimulant |
| 10 | X = CH₃, R = CH₃ | Acute fistula - gastric | ID | Rat | 20 | Marked |
| | | General behavior | IP | Mouse | 10–300 | Weak depressant/ weak stimulant |

TABLE I-continued

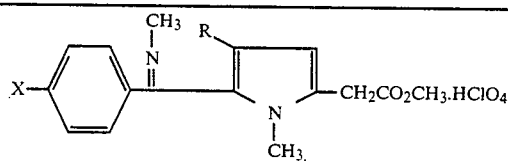

| Compound of Example No. | Above Formula wherein | Screen | Route | Animal | Dose (mg/kg) | Activity |
|---|---|---|---|---|---|---|
| 9 | X = OCH$_3$, R = CH$_3$ | General behavior | IP | Mouse | 2-1000 | Weak depressant/ weak stimulant |

The compounds are prepared through the condensation of imidoyl chlorides of general formula (III):

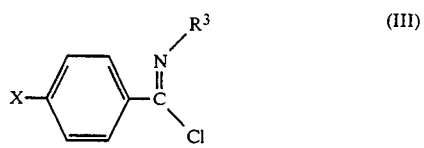

wherein X and R$^3$ are as defined above, with lower alkyl pyrrole-2-acetates of general formula (IV)

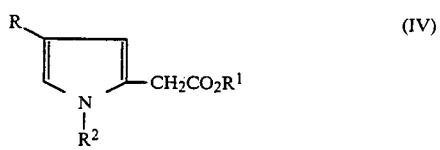

wherein R, R$^1$ and R$^2$ are as defined above, at room temperature. The presence of a catalytic amount of strong protic acid, e.g., H$_2$SO$_4$, HCl, chlorosulfonic acid and the like, or a Lewis acid such as diethyl aluminum chloride may be employed to enhance the rate of the reaction.

Suitable solvents for the condensation are organic aprotic solvents such as aliphatic halogenated hydrocarbons,(e.g., chloroform, methylene chloride, dichloroethane), aromatic hydrocarbons (e.g., benzene, toluene, xylene), aliphatic hydrocarbons (e.g., cyclohexane, pentane, hexane, petroleum ether), and ethereal compounds (e.g., diethyl ether, tetrahydrofuran, glyme); aliphatic halogenated hydrocarbons being preferred, alcohol-free chloroform being the most preferred solvent when using protic acids as the acid catalyst.

The condensation may be run at temperatures in the range of −78° C. to 60° C., the reaction temperature being dependent upon the acid catalyst and reactivity of the imidoyl chloride. In most cases, a reaction temperature of between 10° C. and 30° C. has been shown to be satisfactory. The rate of the reaction has been found to be dependent upon; (1) the substituents on the aromatic ring of the imidoyl halide; (2) the concentration of the imidoyl halide; (3) the concentration of the pyrrole; and (4) the concentration of the acid catalyst. The presence of electron withdrawing groups, e.g., NO$_2$, halide, on the imidoyl halide enhance the reaction rate, while electron donating groups, e.g., OCH$_3$, CH$_3$, reduce the rate of the reaction. Increasing the concentration of imidoyl halide, pyrrole, or the acid catalyst enhances the rate of the reaction, while decreasing the concentration of the imidoyl halide, or acid catalyst reduces the rate of the reaction. Reaction conditions may be found under which the reaction is complete in 2 to 24 hours. In the absence of acid catalysis, the rate of the condensation is negligible.

The title compounds may be isolated by extraction of the crude reaction mixture with aqueous base and concentration of the organic phase. The compounds are typically purified through the preparation of a crystalline salt, e.g., perchlorate or hydrochloride salt.

When used as intermediates in the preparation of 5-aroyl-pyrrole-2-acetic acids, the imines do not need to be isolated and purified.

Hydrolysis of the imidoyl substituted pyrroles claimed herein to 5-aroyl-pyrrole-2-acetic acids or esters may be achieved by direct hydrolysis of the imine in the presence of a base, e.g., sodium acetate, sodium carbonate, sodium bicarbonate, sodium hydroxide, potassium acetate, or potassium bicarbonate in aqueous alcohol. Alternatively, the imine may be hydrolyzed through alkylation of the free base with, for example, dimethyl sulfate, followed by hydrolysis under the above conditions.

The hydrolysis is typically conducted by adding an aqueous solution of the base to a methanolic solution of the imidoyl substituted pyrrole and the resulting solution heated at reflux for a period of time such that hydrolysis of the imine is complete.

The following examples illustrate the present invention without, however, limiting the invention thereto. Examples I–VIII illustrate the preparation of imidoyl chlorides which are used as intermediates to make the imidoyl-substituted-pyrroles of the present invention, as shown in Examples IX–XVIII and XXIV–XXV, which in turn can be used to make the corresponding benzoyl-pyrroles as shown in Examples XX–XXIII. Example XIX illustrates the preparation of the acid by hydrolysis of the unisolated corresponding ester which has been prepared in the initial part of the example.

EXAMPLE I

N-Methyl 4-Methoxybenzimidoyl Chloride

N-Methyl 4-methoxybenzamide (13.95 g, 84.5 mmole) was placed in a 50 ml round bottom flask equipped with magnetic stirrer, heating mantle, condenser and base trap. Thionyl chloride (33 g, 278 mmole) was added. The reaction was stirred and heated at reflux until gas evolution ceased (three hours). The excess thionyl chloride was distilled at ca. 15 mm Hg, and the product distilled at 75°–80° C. (0.1 mm Hg) to yield 11.9 g (76%) of the title compound as a clear colorless liquid.

EXAMPLE II

N-Methyl 4-Methylbenzimidoyl Chloride

N-Methyl 4-methylbenzamide (10.02 g, 67.2 mmole) was treated with thionyl chloride (31.7 g, 267 mmole) as in Example I. Gas evolution ceased after the reaction had been heated for 45 minutes. The product was isolated as in Example I to yield 9.0 g (80%) of the title compound as a clear colorless liquid, b.p. 57° C. (~0.1 mm Hg).

EXAMPLE III

N-Methyl Benzimidoyl Chloride

N-Methyl benzamide (55.97 g., 418 mmole) and thionyl chloride (114.7 g, 0.96 mole) were treated as in Example I. Yield 58.4 g (91%) of the title compound, b.p. 80°-90° C. (~0.1 mm Hg).

EXAMPLE IV

N-Methyl 4-Chlorobenzimidoyl Chloride

N-Methyl 4-chlorobenzamide (42.6 g, 251 mmole) and thionyl chloride (153.3 g, 1.28 mole) were reacted as in Example I to yield 39.3 g (83.4%) of the title compound, b.p. 125° C. (15 mm Hg).

EXAMPLE V

N-Methyl 4-Nitrobenzimidoyl Chloride

N-Methyl 4-nitrobenzamide (30.0 g, 167 mmole) and thionyl chloride (256 g, 2.15 mole) were heated at reflux for five hours. The excess thionyl chloride was removed at ~15 mm Hg. Xylene was added to the reaction and distilled under reduced pressure to yield a solid which was recrystallized from petroleum ether to yield 8.6 g of the title compound as a light yellow solid, m.p. 67°-73° C.

EXAMPLE VI

N-Isopropyl 4-Chlorobenzimidoyl Chloride

N-Isopropyl 4-chlorobenzamide (12.7 g, 64.3 mmole) and thionyl chloride (53.81 g, 447 mmole) were heated at reflux with stirring for two hours. Excess thionyl chloride was removed by distillation. The title compound was isolated by distillation (b.p. 65°-70° C. at ~1 mm Hg) to yield 10.7 g (77%) of a light brown yellow liquid.

EXAMPLE VII

N-Cyclohexyl 4-Chlorobenzimidoyl Chloride

N-Cyclohexyl 4-chlorobenzamide (12.8 g, 53.9 mmole) and thionyl chloride (43.14 g, 363 mmole) were heated at reflux with stirring for 1.75 hours. Excess thionyl chloride was removed by distillation. The title compound was isolated by distillation (b.p. 130° C. at ~15 mm Hg) to yield 7.4 g (54%) of a clear colorless liquid which crystallized upon cooling.

EXAMPLE VIII

N-Octyl 4-Chlorobenzimidoyl Chloride

N-Octyl 4-chlorobenzamide (17.2 g, 64.2 mmole) and thionyl chloride (42.59 g, 358 mmole) were stirred and heated at reflux for one hour. The product was isolated by fractional distillation at reduced pressure (b.p. 70°-90° C. at 15 mm Hg) to yield 14.0 g (77%) of impure title compound.

EXAMPLE IX

Methyl 5-[(4-methoxyphenyl)(methylimino)methyl]-1,4-dimethyl-1H-pyrrole-2-acetate Perchlorate (McN-5387-68)

N-Methyl 4-methoxybenzimidoyl chloride (6.67 g, 36.4 mmole) was placed in a dry 50 ml round bottom flask and treated with alcohol free chloroform (13 ml) and chlorosulfonic acid (0.42 g, 3.6 mmole). The reaction was blanketed with nitrogen and stirred while methyl 1,4-dimethyl-1H-pyrrole-2-acetate (6.03 g., 36.1 mmole) was added dropwise over a period of about five minutes. The reaction was stirred overnight, then heated at 40° C. for two hours. The reaction was quenched with saturated aqueous sodium bicarbonate. The phases were separated, and the organic phase was washed with saturated aqueous sodium bicarbonate and water, then dried over sodium sulfate. The chloroform was removed under reduced pressure to yield a red viscous liquid. The crude product was dissolved in absolute ethanol and treated with 70% perchloric acid (5.7 g, 40 mmole). The solution was cooled and treated with ether to induce crystallization. The yellow solid was isolated by filtration and washed with cold ethanol to yield 10.5 g (64%) of the title compound, m.p. 123°-129° C. (dec).

Elemental analysis, calculated for $C_{18}H_{22}N_2O_3 \cdot HClO_4$: C, 52.12%; H, 5.59%; N, 6.75%; Cl, 8.55%. Found: C, 52.06%; H, 5.59%; N, 6.74%; Cl, 8.53%.

EXAMPLE X

Methyl 1,4-Dimethyl-5-[(methylimino)(4-methylphenyl)methyl]-1H-pyrrole-2-acetate Perchlorate (McN-5373-68)

N-Methyl 4-methylbenzimidoyl chloride (5.44 g, 32.5 mmole) was placed in a dry 50 ml round bottom flask and treated with alcohol free chloroform (13 ml) and chlorosulfonic acid (0.38 g, 3.2 mmole). The reaction was placed under a nitrogen atmosphere and stirred at room temperature. Methyl 1,4-dimethyl-1H-pyrrole-2-acetate (5.39 g, 32.3 mmole) was added and the reaction was stirred overnight. The reaction was quenched with saturated aqueous sodium bicarbonate. The phases were separated, and the organic phase was extracted with saturated aqueous sodium bicarbonate and water, then dried over sodium sulfate. The mixture was filtered and the filtrate was concentrated under reduced pressure. The resulting red-brown viscous liquid was dissolved in absolute ethanol and treated with 70% perchloric acid (5.1 g, 35.5 mmole). The solution was cooled and treated with ether to induce crystallization. The solid was isolated by filtration, washed with cold ethanol, and air dried to yield 7.86 g (61%) of the title compound, m.p. 119°-124° C. (dec).

Elemental analysis, calculated for $C_{18}H_{22}N_2O_2 \cdot HClO_4$: C, 54.21%; H, 5.81%; N, 7.02%; Cl, 8.89%. Found: C, 54.20%; H, 5.84%; N, 7.00%; Cl, 8.89%.

EXAMPLE XI

Methyl 1,4-Dimethyl-5-[(methylimino)phenylmethyl]-1H-pyrrole-2-acetate Perchlorate (McN-5374-68)

The title compound was prepared as in Example X from N-methyl benzimidoyl chloride (6.87 g, 44.8 mmole), chlorosulfonic acid (0.52 g, 4.5 mmole), methyl 1,4-dimethyl-1H-pyrrole-2-acetate (7.43 g, 44.5 mmole), and 70% perchloric acid (7.0 g, 49 mmole) to yield 10.4 g (61%) as a yellow solid, m.p. 145°–147° C. (dec).

Elemental analysis, calculated for $C_{17}H_{20}N_2O_2 \cdot HClO_4$: C, 53.06%; H, 5.50%; N, 7.28%; Cl, 9.21%. Found: C, 52.83%; H, 5.61%; N, 7.12%; Cl, 9.18%.

EXAMPLE XII

Methyl 5-[(4-chlorophenyl)(methylimino)methyl]-1,4-dimethyl-1H-pyrrole-2-acetate Perchlorate (McN-5372-68)

The title compound was prepared as in Example X from N-methyl 4-chlorobenzimidoyl chloride (6.07 g, 32.3 mmole), chlorosulfonic acid (0.46 g, 4.0 mmole), methyl 1,4-dimethyl-1H-pyrrole-2-acetate (6.64 g, 39.8 mmole), and 70% perchloric acid (5.5 g, 38.3 mmole) to yield 9.3 g (69%) of a bright yellow solid, m.p. 168°–171° C. (dec).

Elemental analysis, calculated for $C_{17}H_{19}ClN_2O_2 \cdot HClO_4$: C, 48.70%; H, 4.81%; N, 6.68%; Cl, 16.91%. Found: C, 48.65%; H, 4.81%; N, 6.68%; Cl, 16.89%.

EXAMPLE XIII

Methyl 1,4-Dimethyl-5-[(methylimino)(4-nitrophenyl)methyl]-1H-pyrrole-2-acetate Perchlorate (McN-5389-68)

The title compound was prepared as in Example X from N-methyl 4-nitrobenzimidoyl chloride (2.0 g, 10.1 mmole) in alcohol free chloroform (30 ml), chlorosulfonic acid (0.12 g, 1 mmole), methyl 1,4-dimethyl-1H-pyrrole-2-acetate (1.68 g, 10.06 mmole) and 70% perchloric acid (1.57 g, 11 mmole) to yield 2.77 g (65%) of a yellow solid, m.p. 108° C. (dec).

Elemental analysis, calculated for $C_{17}H_{19}N_3O_4 \cdot HClO_4$: C, 47.51%; H, 4.69%; N, 9.78%; Cl, 8.25%. Found: C, 47.53%; H, 4.71%; N, 9.75%; Cl, 8.28%.

EXAMPLE XIV

Methyl 1-Methyl-5-[(methylimino)(4-methylphenyl)methyl]-1H-pyrrole-2-acetate Perchlorate (McN-5388-68)

The title compound was prepared as in Example X from N-methyl 4-methylbenzimidoyl chloride (5.9 g, 35 mmole), chlorosulfonic acid (0.41 g, 3.5 mmole), methyl 1-methyl-1H-pyrrole-2-acetate (5.4 g, 35 mmole), and 70% perchloric acid (5.5 g, 38.5 mmole) to yield 4.0 g (30%) of a green solid, m.p. 155°–159° C. (dec).

Elemental analysis, calculated for $C_{17}H_{20}N_2O_2 \cdot HClO_4$: C, 53.06%; H, 5.50%; N, 7.28%; Cl, 9.21%. Found: C, 53.07%; H, 5.50%; N, 7.26%; Cl, 9.22%.

EXAMPLE XV

Methyl 5-[(4-chlorophenyl)(isopropylimino)methyl]-1,4-dimethyl-1H-pyrrole-2-acetate Perchlorate The title compound was prepared as in Example X from N-isopropyl 4-chlorobenzimidoyl chloride (10.75 g, 49.8 mmole), chlorosulfonic acid (0.58 g, 5.0 mmole), methyl 1,4-dimethyl-1H-pyrrole-2-acetate (8.34 g, 50 mmole), and 70% perchloric acid (7.8 g, 55 mmole) to yield 14.2 g (64%) of a bright yellow solid, m.p. 94°–110° C. (dec).

EXAMPLE XVI

Methyl 5-[(4-chlorophenyl)(cyclohexylimino)methyl]-1,4-dimethyl-1H-pyrrole-2-acetate Perchlorate The title compound was prepared as in Example X from N-cyclohexyl 4-chlorobenzimidoyl chloride (7.4 g, 29 mmole), chlorosulfonic acid (0.34 g, 3 mmole), methyl 1,4-dimethyl-1H-pyrrole-2-acetate (4.82 g, 28.86 mmole), and 70% perchloric acid (4.6 g, 32 mmole) to yield 1.97 g (14%) of a lime green solid, m.p. 196°–202° C. (dec).

EXAMPLE XVII

Methyl 5-[(4-chlorophenyl)(octylimino)methyl]-1,4-dimethyl-1H-pyrrole-2-acetate Perchlorate The title compound was prepared as in Example X from N-octyl 4-chlorobenzimidoyl chloride (1.44 g, 5 mmole), chlorosulfonic acid (0.58 g, 0.5 mmole), methyl 1,4-dimethyl-1H-pyrrole-2-acetate (0.84 g, 5 mmole), and 70% perchloric acid (0.79 g, 5.5 mmole) to yield 1.99 g (77%) of a red viscous oil.

EXAMPLE XVIII

Ethyl 5-[(4-chlorophenyl)(methylimino)methyl]-1,4-dimethyl-1H-pyrrole-2-acetate Perchlorate The title compound was prepared as in Example X from N-methyl 4-chlorobenzimidoyl chloride (7.52 g, 40 mmole), chlorosulfonic acid (0.47 g, 4 mmole), ethyl 1,4-dimethyl-1H-pyrrole-2-acetate (7.25 g, 40 mmole), and 70% perchloric acid (7.0 g, 48 mmole) to yield 6.6 g (38%) of a green solid, m.p. 126°–130° C. (dec).

EXAMPLE XIX

5-[(4-chlorophenyl)(methylimino)methyl]-4-methyl-1H-pyrrole-2-acetic acid

N-Methyl 4-chlorobenzimidoyl chloride (2.37 g, 12.6 mmole) was placed in a dry 50 ml round bottom flask and treated with alcohol free chloroform and chlorosulfonic acid (0.15 g, 1.3 mmole). The reaction was placed under a nitrogen atmosphere and stirred at room temperature while ethyl 4-methyl-1H-pyrrole-2-acetate (2.11 g, 12.6 mmole) was added dropwise over a five-minute period. Upon addition of the pyrrole, the reaction mixture turned dark brown and the reaction temperature rose. The reaction was stirred overnight at room temperature, then quenched with saturated aqueous sodium bicarbonate. The phases were separated and the organic phase was extracted with saturated aqueous sodium bicarbonate, washed with water, dried over sodium sulfate, filtered, and concentrated. The residue was dissolved in absolute ethanol, treated with 70% perchloric acid (2.0 g, 14 mmole) cooled and diluted with ether. A brown viscous liquid separated which was suspended in methylene chloride and treated with saturated aqueous sodium bicarbonate. The solution was dried over sodium sulfate, filtered, and concentrated. The residue was placed on a silica gel column and eluted with methylene chloride/methanol (99/1) to remove nonpolar impurities. The silica gel was extracted with methanol to yield 0.47 g (12%) of the title compound as a dark brown solid, m.p. 79°–80° C. (dec).

EXAMPLE XX

Methyl 1-Methyl-5-(4-methylbenzoyl)-1H-pyrrole-2-acetate (McN-2775)

N-Methyl 4-methylbenzimidoyl chloride (3.85 g, 23 mmole) was treated with alcohol free chloroform (4.5 ml) and chlorosulfonic acid (0.2 g, 1.7 mmole). Methyl 1-methyl-1H-pyrrole-2-acetate (3.5 g, 23 mmole) was added in one portion, the reaction was fitted with a calcium chloride drying tube and stirred overnight. The reaction was quenched with saturated aqueous sodium bicarbonate. The phases were separated and the organic phase was concentrated under reduced pressure. The residue (6.6 g of a red oil) was dissolved in methanol (50 ml) and treated with sodium acetate (3 g, 36 mmole) and water (10 ml). The reaction was heated at reflux overnight, then cooled in an ice bath. The title compound crystallized and was isolated by filtration, washed with cold methanol, and air dried to yield 2.3 g (37%) of a light tan solid, m.p. 117°–119° C.

EXAMPLE XXI

Methyl 5-(4-chlorobenzoyl)-1,4-dimethyl-1H-pyrrole-2-acetate (McN-5091)

Methyl 5-[(4-chlorophenyl)(methylimino)methyl]-1,4-dimethyl 1H-pyrrole-2-acetate perchlorate (0.37 g, 0.9 mmole) was treated with sodium acetate (1.1 g, 13 mmole), acetic acid (0.37 g, 6 mmole), methanol (19 ml) and water (1 ml). The reaction was heated at reflux for one week, then poured into water, and extracted with chloroform. The chloroform extracts were washed with water, dried over sodium sulfate, filtered and concentrated. The residue was dissolved in a minimum amount of methylene chloride and eluted through a short plug of silica gel to remove polar impurities. The solvent was removed under reduced pressure to yield 0.17 g (62%) of the title compound as a light tan solid, m.p. 122°–125° C.

EXAMPLE XXII

Methyl 5-(4-chlorobenzoyl)-1,4-dimethyl-1H-pyrrole-2-acetate (McN-5091)

Methyl 5-[(4-chlorophenyl)(methylimino)methyl]-1,4-dimethyl-1H-pyrrole-2-acetate perchlorate (1.5 g, 3.6 mmole) was treated with saturated aqueous sodium bicarbonate and extracted with chloroform (50 ml). The organic phase was dried over magnesium sulfate, filtered and concentrated. The residue was treated with dimethyl sulfate (0.62 g, 4.9 mmole) and heated at ~40° C. for one hour. The viscous reaction mixture was dissolved in methanol (10 ml) and treated with sodium acetate (2 g, 24 mmole) and water (2 ml) and heated at reflux overnight. The reaction was cooled and diluted with water (5 ml). The crystalline solid was isolated by filtration, washed with water, air dried, and recrystallized from methanol (10 ml) to yield 0.71 g (65%) of the title compound as a tan solid, m.p. 125°–131° C.

EXAMPLE XXIII

Sodium 5-(4-chlorobenzoyl)-1,4-dimethyl-1H-pyrrole-2-acetate Dihydrate (McN-2783-21-98)

Methyl 5-[(4-chlorophenyl)(methylimino)methyl]-1,4-dimethyl-1H-pyrrole-2-acetate perchlorate (1.5 g, 3.6 mmole) was dissolved in chloroform, extracted with saturated aqueous sodium bicarbonate, dried over sodium sulfate, and concentrated. The residue was treated with dimethyl sulfate (0.5 g, 3.9 mmole) and allowed to stand at 18°–30° C. for two hours. The reaction was dissolved in methanol (10 ml) and treated with saturated aqueous sodium bicarbonate (5 ml) and water (2 ml). The solution was heated at reflux overnight, then allowed to cool to room temperature. The solid was isolated by filtration, washed with water, and air dried to yield 0.95 g (76%) of the title compound as a light tan solid, m.p. >230° C.

EXAMPLE XXIV

Methyl 1,4-Dimethyl-5-[(methylimino)phenylmethyl]-1H-pyrrole-2-acetate Perchlorate (McN-5374-68)

Methyl 1,4-dimethyl-1H-pyrrole-2-acetate (1.66 g, 10 mmole) was placed in a 25 ml round bottom flask and treated with alcohol free chloroform (2 ml) and N-methyl benzimidoyl chloride (1.78 g, 12 mmole). The solution was treated with several drops of ethereal hydrogen chloride—mild exotherm. The reaction was protected with a calcium chloride drying tube and stirred at room temperature for about four hours. The reaction was diluted with chloroform, quenched into saturated sodium bicarbonate, washed with brine, dried over sodium sulfate, filtered and concentrated. The viscous residue was dissolved in absolute ethanol (6 ml) and treated with 70% perchloric acid (1.42 g, 10 mmole). The resulting crystalline solid was isolated by filtration and washed with ethanol/ether (1 to 3 by volume) and air dried to yield 2.39 g (62%) of the title compound as a bright yellow solid, m.p. 149°–150° C.

EXAMPLE XXV

Methyl 1,4-Dimethyl-5-[(methylimino)phenylmethyl]-1H-pyrrole-2-acetate Perchlorate (McN-5374-68)

Methyl 1,4-dimethyl-1H-pyrrole-2-acetate (1.67 g, 10 mmole) and alcohol free chloroform (20 ml) were placed in a 50 ml round bottom flask, placed under a nitrogen atmosphere, and cooled in a dry ice/acetone bath. Diethylaluminum chloride (10 ml of a 1 M hexane solution, 10 mmole) was added, and the reaction was stirred and allowed to warm to room temperature. After three hours, the reaction was carefully poured into aqueous ammonium chloride. The aqueous phase was extracted with methylene chloride. The combined organic extracts were extracted with ammonium chloride solution and saturated sodium bicarbonate, dried over magnesium sulfate, filtered and concentrated. The residue was dissolved in ethanol (5 ml) and treated with 70% perchloric acid (1.47 g, 10 mmole). A yellow solid crystallized and was isolated by filtration, washed with ethanol, and air dried to yield 2.0 g (52%) of the title compound, m.p. 148°–149° C.

I claim:

1. An aryl-pyrrolyl-imine derivative compound having the formula

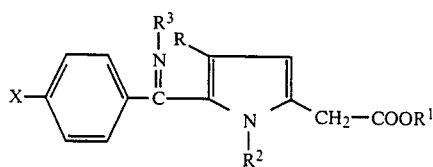

(I)

and the acid addition salts thereof, wherein X is H, NO$_2$, halo, lower alkyl, or lower alkoxy; R is H or methyl; R$^1$ is H or lower alkyl; R$^2$ is H or lower alkyl; and R$^3$ is C$_{5-8}$ cyclic lower alkyl.

2. A compound, according to claim 1, wherein in the formula X is H or Cl or CH$_3$, R is H or CH$_3$, R$^1$ is CH$_3$, R$^2$ is CH$_3$, and R$^3$ is cyclohexyl.

3. A compound according to claim 1 which is methyl 5-[(4-chlorophenyl)(cyclohexylimino)methyl]-1,4-dimethyl-1H-pyrrole-2-acetate or an acid addition salt thereof.

4. A compound according to claim 2 wherein the acid addition salt is the perchlorate.

5. A compound according to claim 1, wherein R is CH$_3$.